United States Patent [19]
Zaneveld et al.

[11] Patent Number: 5,932,619
[45] Date of Patent: Aug. 3, 1999

[54] METHOD FOR PREVENTING SEXUALLY TRANSMITTED DISEASES

[75] Inventors: Lourens Jan Dirk Zaneveld; Robert Anthony Anderson, Jr.; Xiao Hui Diao, all of Chicago; Paul Robert Young, Jr., Oak Park; Donald Paul Waller, Oakbrook; Sanjay Garg, Chicago; Calvin J. Chany, II, Bolingbrook; Darrick S. H. L. Kim, Chicago, all of Ill.

[73] Assignee: Rush-Presbyterian, St. Luke's Medical Center, Chicago, Ill.

[21] Appl. No.: 08/965,935

[22] Filed: Nov. 7, 1997

Related U.S. Application Data

[63] Continuation-in-part of application No. 08/729,742, Oct. 7, 1996
[60] Provisional application No. 60/005,412, Oct. 13, 1995.
[51] Int. Cl.⁶ ................................................ A61K 37/10
[52] U.S. Cl. ............................................ 514/570; 514/571
[58] Field of Search ..................................... 514/570, 571

[56] References Cited

U.S. PATENT DOCUMENTS

| | | | |
|---|---|---|---|
| 5,166,173 | 11/1992 | Hwang et al. | 514/510 |
| 5,196,452 | 3/1993 | Hwang et al. | 514/577 |
| 5,312,837 | 5/1994 | Hwang et al. | 514/577 |
| 5,441,983 | 8/1995 | Hwang et al. | 514/562 |
| 5,605,930 | 2/1997 | Samid | 514/510 |

OTHER PUBLICATIONS

Rogers, H. J., et al., (1954) "Synthetic Polyanionic Inhibitors of Hyaluronidase", *Biochim. Biophys. Acta* 13: 293–294.
Beiler, J. M., et al., (1948) "Inhibition of Hyaluronidase Action By Derivatives of Hesperidin", *J. Bio. Chem.*, 174:31–34.
Joyce, C. L., et al., (1986) "Effect of Hyaluronidase β–Glucuronidase and β–N–Acetylglucosaminidase Inhibitors on Sperm Penetration of the Mouse Oocyte", *Biol Reprod.*, 35:336–346.
Sieve, F., (1952) "A new antifertility factor." *Science*, 116:373–385.
Chang, M. C., et al., (1953) "Does Phosphorylated Hesperidin Affect Fertility?" *Science*, 117:274–276.
Thompson, R. Q., et al., (1953) "Effect of phosphorylated hesperidin and other flavonoids on fertility in mice.", *Science*, 118:657.
Foldesy, R. G., et al., (1986), "Multiple actions of a novel vaginal contraceptive compound", ORF 13904. *Fert*.
Won Hahn, D., et al. (1986), "Prototype of a new long–acting spermistatic agent", *Male Contraception: Advanced and Future Prospects*, Harper & Row, Hagerstown, pp. 218–226.
Mohan, P., (1992), "Anti–AIDs Development: Challenges and Strategies", *Pharmaceutical Research*, vol. 9, No. 6, pp. 703–714.
Parkes, A. S., et al. (1954) "Biological and Biochemical Aspects for the Prevention of Fertilization By Enzyme Inhibitors", *Proc. Soc. Study Fertility*, 6:65–80.
Joyce, C. L., et al., (1985) "Vaginal contraceptive activity of hyaluronidase and cyclooxygenase (prostaglandin synthetase) inhibitors in the rabbit", *Fertil. Steril.*, 44:426–428.
Joyce, C. L., et al., (1979) "Contraceptive Effects of Intravaginal Application of Acrosin and Hyaluronidase Inhibitors in Rabbit", *Contraception*, 19(1):95–106.
Martin, G. J., et al., (1952) "Effect of Phosphorylated Hesperidin, a Hyaluronidase Inhibitor, on Fertility in the Rat", *Science*, I 1 5:402.
Wang et al. 111CA:50541h, 1989.

*Primary Examiner*—Russell Travers
*Attorney, Agent, or Firm*—Fitch, Even, Tabin & Flannery

[57] ABSTRACT

A method for the reduction in the risk of transmitting a sexually transmitted disease—especially HIV and/or HSV—during sexual activity is provided. This method generally comprises the application of an effective amount of an inhibitory agent, preferably as a topical formulation, to the area or areas of sexual contact prior to engaging in sexual activity. Inhibitory agents which are useful in the present invention include, for example, phosphorylated hesperidins, sulfonated hesperidins, polystyrene sulfonates, substituted benzenesulfonic acid formaldehyde co-polymers, $H_2SO_4$-modified mandelic acids, and the like. This method can be used by heterosexuals, homosexuals, and/or bisexuals engaged in a wide variety of sexual activities. In addition to anti-STD activity, these agents may also act as vaginal contraceptives; moreover, they generally have fewer side effects than conventional vaginal contraceptives (e.g., nonoxynol-9). For example, the compounds useful in this invention are generally not toxic to natural and beneficial vaginal flora and, thus, do not upset the local microbiological balance. The anti-STD method of the present invention has the added advantage that it can be implemented and controlled by either sexual party. Methods are also provided for reducing the risk of transmission of STD-causing organisms to health care providers and laboratory personnel (or other persons) who may come into contact with biological samples and specimens.

26 Claims, No Drawings

METHOD FOR PREVENTING SEXUALLY TRANSMITTED DISEASES

RELATED APPLICATION

This application is a continuation-in-part of U.S. application Ser. No. 08/729,742, filed Oct. 7, 1996, which was based on, and claimed benefit of, U.S. Provisional application Ser. No. 60/005,412, filed on Oct. 13, 1995.

FIELD OF THE INVENTION

This invention generally relates to a method for preventing sexually transmitted diseases (STDs) and/or reducing the rate of transmission of such sexually transmitted diseases. This method can be used by heterosexual, homosexual, and bisexual individuals to significantly reduce the risk of being infected by, or of transmitting, a sexually transmitted disease through sexual contact. The present method is especially effective for reducing the risk of transmission of human immunodeficiency virus (HIV) and herpes simplex virus (HSV). The risk of transmission of other sexually transmitted diseases may also be reduced. The present method of this invention is especially effective when used in conjunction with so-called "safe sex" techniques. This method can also be used by health-care providers or others to reduce their risk of being infected by such STDs through contact with bodily fluids of STD-infected patients (especially HIV/AIDS patients).

In one embodiment, the method of this invention generally comprises the application of an effective amount of an inhibitory agent, preferably as a topical formulation, to the area or areas of sexual contact prior to engaging in sexual activity. Inhibitory agents which are useful in the present invention include, for example, phosphorylated hesperidins, sulfonated hesperidins, polystyrene sulfonates, substituted benzenesulfonic acid formaldehyde co-polymers, $H_2SO_4$-modified mandelic acids, and the like. It appears that these inhibitory agents primarily act by inhibiting the STD-cell organisms rather than killing them (i.e., the inhibitory agents are generally noncytotoxic relative to the STD-causing organisms). Of course, as one skilled in the art will realize, these inhibitory agents may act as cytotoxic agents if present in higher concentrations. In addition to anti-STD activity, these inhibitory agents may also act as vaginal contraceptives; moreover, they generally have fewer side effects than conventional vaginal contraceptives (e.g., nonoxynol-9). For example, the compounds useful in this invention are generally not toxic (or only slightly toxic) at their effective levels to natural and beneficial vaginal flora and, thus, do not significantly upset the local microbiological balance. The anti-STD method of the present invention has the added advantage that it can be implemented and controlled by either sexual party.

In another embodiment, the method of this invention generally comprises the application of an effective amount of an inhibitory agent to the area or areas of an individual likely to come in contact, or which have come in contact, with bodily fluids from a person who may be infected with a sexually transmitted disease. This embodiment is expected to be especially useful to health care providers and/or laboratory personnel working with HIV/AIDS patients and/or blood or tissue samples from such patients. Inhibitory agents which are useful in the present invention include, for example, phosphorylated hesperidins, sulfonated hesperidins, polystyrene sulfonates, substituted benzenesulfonic acid formaldehyde co-polymers, $H_2SO_4$-modified mandelic acids, and the like. This method is not intended to replace prudent health-care or laboratory procedures but is rather intended to offer supplemental protection in cases where the risk of exposure is present or in cases where exposure actually occurs.

BACKGROUND OF THE INVENTION

In recent years, sexually transmitted diseases have become an increasing medical problem and concern throughout the world. The HIV/AIDS epidemic over the last decade or so has significantly and dramatically underscored the threat of STDs to the human population. Until there is a cure, or at least an effective treatment, the best, and perhaps only realistic, approach to this increasing problem of STDs (especially HIV/AIDS) appears to be reducing the risk of transmission of STDs by the STD-causing organisms and thus reducing the number of individuals who become newly infected. Even when treatments or cures become available, prevention of infections in the initial instance will likely remain as the first line of defense. For both economic and medical reasons, it is preferable to prevent the initial infection rather than treating, and even curing, individuals with STDs.

At present, education in regard to STDs, their modes of transmission, and so-called "safe-sex" techniques has, at least to some degree in the more developed countries, shown promise in reducing the risks of STD transmission through sexual activity. Screening of the blood supply has helped to reduce the risk of transmission of such STD-causing organisms via blood transfusions and related medical practices. Nonetheless, the spread of such STDs has not been halted to a satisfactory degree even in developed countries with active and progressive education programs. Even with their known effectiveness in preventing STDs, current safe-sex techniques are not always used, or are not always used properly, for many reasons (e.g., carelessness, lack of knowledge, improper techniques, cultural barriers, unplanned or spontaneous sexual activity, and the like). Moreover, even when used, safe-sex techniques (except perhaps abstinence) are not always effective. For example, condoms are generally only about 90 percent effective in preventing conception when used alone; in the case of such failures, STD-causing organisms, if present, may pass from one sexual partner to the other.

Various birth control devices—including barrier methods and vaginal contraceptives—are currently available. Some of these may, in addition, also have a least some degree of anti-STD activity. For example, condoms can help prevent the transmission of STDs so long as they are properly used and/or they perform properly. Nonoxynol-9, currently one of the most widely used contraceptive agents, is reported, at least in some cases, to reduce the risk of transmission of some STDs. Nonoxynol-9, which is a nonionic detergent with strong surfactant properties, acts, like most other chemical-based contraceptives, by killing or otherwise immobilizing spermatozoa (e.g., spermicidal activity). Nonoxynol-9 is a potent cytotoxic agent which tends to nonspecifically disrupt cell membranes. These properties, however, give rise to some very significant disadvantages. Because nonoxynol-9 is strongly cytotoxic, it can injure vaginal/cervical epithelial and other cells at concentrations as low as about 0.0005 percent. Clinical studies have confirmed epithelial disruption of the vagina and cervix. Nonoxynol-9 also disrupts the normal vaginal flora which provides a protective mechanism, perhaps by maintaining a low pH, to guard against the invasion of pathogenic microbes. Nonoxynol-9 may also partially dissolve or remove the protective glycoprotein coating in the vagina.

The cytotoxic, flora-disruptive, and glycoprotein-removal effects of nonoxynol-9 can lead to vaginal damage or injury, including lesions. Some women are especially sensitive to nonoxynol-9 and manifest these effects with only occasional use. The disruption of these protective mechanisms by nonoxynol-9 can actually increase the risks of STD since the breakdown of the protective mechanisms, and especially the occurrence of lesions, allows STD-causing organisms an easier pathway into the cells. Thus, any anti-STD activity of the contraceptive may be reduced or even lost (i.e., overwhelmed) by the increased risk of infection due to physical damage from the contraceptive. Even if such a contraceptive method provided some degree of STD protection, it would, of course, mainly be directed at heterosexual relationships in which pregnancy was not desired.

It would be desirable, therefore, to provide improved methods for reducing the risk of STD infections during sexual activity. It would be desirable if such methods would not interfere with the natural and protective vaginal mechanisms. It would also be desirable if such methods would be relatively easy to use and have significantly fewer side effects than currently available methods (i.e., nonoxynol-9) so that it would more likely be used on a consistent basis. It would also be desirable if such methods could be used in heterosexual, homosexual, and bisexual relationships and for a wide range of sexual activities. It would also be desirable if such methods could be implemented by either party to the sexual activity. The present invention, as detailed in the present specification, provides such methods.

Such sexually transmitted diseases, especially HIV/AIDS, also present risks to health care providers and laboratory personnel working with STD-infected patients and/or blood and tissue samples from such patients. Physical contact with the bodily fluids of infected patients can, especially if there are breaks or cuts in the skin, increase the risk of transmission of the STD-causing organisms. In recent years, such health care providers and laboratory personnel have increasingly donned protective clothing and equipment when working with patients or biological samples where exposure to bodily fluids is possible. Latex gloves (often double or triple layered), goggles, protective clothing, and the like are often used when treating or examining patients in both medical and dental offices or working with biological samples from patients (e.g., blood, tissue, and the like). In spite of these precautions, exposure to bodily fluids can still occur. For example, sudden movement by a patient while having a blood sample withdrawn can cause blood to splatter and, perhaps, come in contact with an unprotected part of the body of other persons in the area; needle punctures or scalpel cuts can expose health-care providers to bodily fluids in spite of gloves and other protective layers; or aerosols containing blood and/or saliva can be generated during dental procedures which may contact the body of other persons. Although contact with unbroken and healthy skin is unlikely to result in transmission of the STD, breaks, cuts, or damage to the protective skin layer can increase the risk of transmission. It would, therefore, also be desirable to provide methods by which the risk of infection by sexually transmitted diseases, especially HIV/AIDS, could be reduced for individual working with patients and/or biological samples. The present invention, as detailed in the present specification, provides such methods.

SUMMARY OF THE INVENTION

This invention generally relates to a method for preventing STDs and/or reducing the risk of transmission of such STDs through sexual activity. This method is suitable for use by heterosexual, homosexual, and bisexual individuals to significantly reduce the risk of being infected by, or of transmitting, a STD through sexual contact. Although this method can be used alone, it is generally preferred that it be used in conjunction with other so-called "safe sex" techniques in order to even further reduce the risk of STD transmission or infection.

The method of this invention generally comprises the application of an effective amount of an inhibitory agent to the area or areas of sexual contact (e.g., genitalia) of at least one (and preferably all) of the participants prior to engaging in sexual activity. For purposes of this invention an "inhibitory agent" is a compound or mixture of compounds which can inactivate at least one major STD-causing organisms (HIV, HSV, gonococci, and/or chlamydia) without necessarily killing them. Inhibitory agents which are useful in the present invention include, for example, phosphorylated hesperidins, sulfonated hesperidins, polystyrene sulfonates, substituted benzenesulfonic acid formaldehyde co-polymers, $H_2SO_4$-modified mandelic acids, and the like. Preferably the inhibitory agents used in the present invention are at least partially water soluble or water dispersable so that anti-STD formulations can more easily be prepared.

In addition to anti-STD activity, these compounds may also act as vaginal contraceptives and generally have fewer side effects than conventional vaginal contraceptives (e.g., nonoxynol-9). For example, the compounds useful in this invention are generally not toxic (or only minimally toxic) to natural and beneficial vaginal flora and, thus, do not significantly upset the local microbiological balance or significantly disrupt the protective glycoprotein vaginal coating. Disruption of the natural vaginal flora and/or removal or disruption of the protective glycoprotein vaginal coating using conventional vaginal contraceptives can lead to irritation of the vaginal wall and/or lesions on the vaginal wall which can make the transmission of STD easier and/or more likely. In addition, the compounds useful in this invention are generally not disruptive to rectal tissue and should not, therefore, significantly contribute to the formation of lesions or breaks in the rectal lining which could increase the risk of STD transmission during anal intercourse.

Either party to the sexual contact can employ the method of the present invention in order to protect him or herself and their partners. This feature allows either party to take protective measures without relying on the motivation or action of the other party. Of course, the highest level of protection is obtained when both or all parties take appropriate steps to practice the methods of this invention in conjunction with "safe-sex" techniques.

One object of the present invention is to provide a method for reducing the risk of transmission and infection by a sexually transmitted disease through sexual activity between two or more parties, said method comprising applying an effective amount of an inhibitory agent to an area of the body to be engaged in the sexual activity of at least one of the parties prior to the sexual activity and then engaging in the sexual activity, wherein the inhibitory agent is selected from the group consisting of phosphorylated hesperidins, sulfonated hesperidins, polystyrene sulfonates, substituted benzenesulfonic acid formaldehyde co-polymers, and $H_2SO_4$-modified mandelic acids.

Another object of the present invention is to provide a method for reducing the risk of transmission and infection by a sexually transmitted disease through sexual activity between two or more parties, said method comprising administering an effective amount of an inhibitory agent to the area or areas of body of one or more of the parties in sexual contact during the sexual activity before or after the sexual activity, wherein the inhibitory agent is selected from the group consisting of phosphorylated hesperidins, sulfonated hesperidins, polystyrene sulfonates, substituted benzenesulfonic acid formaldehyde co-polymers, and $H_2SO_4$-modified mandelic acids.

Another object of the present invention is to provide a method for reducing the risk of transmission and infection by a sexually transmitted disease through sexual activity between two or more parties, said method comprising applying an effective amount of an inhibitory agent to an area or areas of the body to be engaged in the sexual activity of at least one of the parties prior to the sexual activity, then engaging in the sexual activity, and then applying an additional amount of the inhibitory agent to the area or areas which was engaged in the sexual activity, wherein the inhibitory agent is selected from the group consisting of phosphorylated hesperidins, sulfonated hesperidins, polystyrene sulfonates, substituted benzenesulfonic acid formaldehyde co-polymers, and $H_2SO_4$-modified mandelic acids.

Still another object of the present invention is to provide a method for reducing the risk of transmission and infection by a sexually transmitted disease through sexual activity between two parties wherein the first party is a male and the second party is a male or female and the sexual activity involves the penis of the first party, said method comprising applying a condom to the penis of the first party, applying an effective amount of an inhibitory agent to an area of the body of the second party which is to be engaged in the sexual activity or to the condom of the first party prior to the sexual activity, and then engaging in the sexual activity, wherein the inhibitory agent is selected from the group consisting of phosphorylated hesperidins, sulfonated hesperidins, polystyrene sulfonates, substituted benzenesulfonic acid formaldehyde co-polymers, and $H_2SO_4$-modified mandelic acids.

Still another object of the present invention is to provide a method for preventing or reducing the risk of pregnancy through sexual activity between a male and a female, said method comprising applying an effective amount of a $H_2SO_4$-modified mandelic acid to either the male or female in such a manner that sperm from the male are exposed to the $H_2SO_4$-modified mandelic acid before they can contact the egg or eggs of the female, wherein the exposure to the $H_2SO_4$-modified mandelic acid is for a sufficient time to prevent or reduce the risk of pregnancy. Preferably, the $H_2SO_4$-modified mandelic acid is contained in an inert carrier at a concentration greater than about 5 mg/g, and even more preferably at a concentration of about 10 to 200 mg/g. Preferably, a male or female condom is also used with the $H_2SO_4$-modified mandelic acid treatment to even further reduce the risk of pregnancy.

In a second embodiment, this invention also relates to methods for reducing the risk of transmission of STDs, especially HIV/AIDS, to health care providers or other individuals working with potentially infected patients and/or individuals obtaining, handling, working with, or disposing of biological samples and/or specimens from potentially infected patients. Thus, still another object of this present invention is to provide a method for reducing the risk of transmission of a sexually transmitted disease to an uninfected individual through contact with the bodily fluids of a potentially sexually transmitted disease infected person, said method comprising applying to the body or portion of the body of the uninfected individual an effective amount of an inhibitory agent at a time prior to likely contact with the bodily fluids or at a time as soon as possible after actual contact with the bodily fluids, wherein the inhibitory agent is selected from the group consisting of phosphorylated hesperidins, sulfonated hesperidins, polystyrene sulfonates, substituted benzenesulfonic acid formaldehyde co-polymers, and $H_2SO_4$-modified mandelic acids.

These and other objects and advantages of the present invention will be apparent from a consideration of the present specification.

DETAILED DESCRIPTION OF THE INVENTION

A method is provided for reducing the rate or probability of transmission of sexually transmitted diseases between sexual partners when one or more of the partners is infected. Of course, the present method is not limited to use by sexual partners where one of the partners is known to be infected by a STD or at risk for a STD. Rather, this method can be used by sexual partners where neither has a known STD, where one partner has a STD or is at risk for a STD, or where both partners have STDs or are at risk for STDs. Because STDs can be transmitted by an infected partner even before symptoms appear in that party, it is generally recommended that this method be used consistently by sexually active individuals. Since no one method of preventing the transmission of STDs—except perhaps complete avoidance of sexual activity—is one hundred percent effective, the present method is preferably practiced in conjunction with other methods of reducing the probability of transmission of STDs. For example, the present method can be combined with the use of condoms (male or female) and other safe-sex techniques to significantly improve the overall effectiveness as compared to the use of either method alone; such combined methods could go a long way towards eliminating or, at least, significantly reducing the transmission of STDs from one sexual partner to another.

The method of the present invention is carried out by applying an effective amount of an inhibitory compound to the area or areas expected to undergo sexual contact during the sexual activity, especially to those areas in which the transmission of STD-causing organisms is more likely and which will likely be in contact with a partner's bodily fluids which may contain the STD-causing organisms. For purposes of this invention, an "effective amount of an inhibitory compound or agent" is an amount sufficient to inactivate, but not necessarily kill, STD-causing organisms on contact. Suitable inhibitory compounds or agents for use in the present invention include, for example, phosphorylated hesperidins, sulfonated hesperidins, polystyrene sulfonates, substituted benzenesulfonic acid formaldehyde co-polymers, $H_2SO_4$-modified mandelic acids, and the like.

Generally, these inhibitory compounds are incorporated into conventional carriers, such as, for example, lotions, creams, jellies, liniments, ointments, salves, oils, foams, gels, washes, suppositories, slow-releasing polymers, coatings, or devices, and the like so that they can be easily applied topically in the present methods. The carriers may also include other ingredients such as, for example, pH modifiers, stabilizers, buffers, surfactants, moisturizers, colorants, thickeners, flavorings, fragrances, perfumes, and the like. The inhibitory agents of the present invention may also be used with conventional birth-control or safe-sex devices. For example, the inhibitory agents could be incorporated into or simply used in conjunction with condoms (i.e., via lubricants applied to the interior and/or exterior surfaces), diaphragms, cervix caps, or similar products. The inhibitory agents of the present invention could also, for example, be released into the vagina (or rectum in the case of anal intercourse) by hand, via suppositories, or by using conventional tampon or syringe techniques. The method of administering or delivering the inhibitory agents to the potential STD-transmission site is not critical so long as an effective amount of the inhibitory agent is delivered to the site in a timely manner. Preferably the formulations and/or method of delivering the inhibitory agents allows the inhibitory agents to remain in the appropriate area during (and even after) the sexual activity in order to maximize the effectiveness.

Preferred inhibitory agents include phosphorylated hesperidins, sulfonated hesperidins, polystyrene sulfonates, substituted benzenesulfonic acid formaldehyde co-polymers, and $H_2SO_4$-modified mandelic acids. The most preferred substituted benzenesulfonic acid formaldehyde co-polymers are the hydroquinone sulfonic acid formaldehyde co-polymers. Preferably the inhibitory agents used are water soluble or dispersable (or at least partially so). Generally, the inhibitory agents are employed at a concentration of about 5 mg/g or higher in a suitable formulation, preferably at a concentration of about 10 mg/g to about 200 mg/g, and more preferably at a concentration of about 20 mg/g to about 100 mg/g based on the total weight of inert and active ingredients. Although it is generally preferred that such anti-STD compounds be used at noncytotoxic levels in order to minimize potential side effects, these compounds can also be used, if desired, at levels at which the STD-organisms (or a significant portion thereof) are effectively killed rather than simply inactivated or inhibited.

In actual use, the inhibitory agent in a suitable carrier or vehicle is applied, preferably topically, to the general area or areas of expected sexual contact (e.g., areas in which bodily fluids are likely to be generated and/or deposited) prior to the sexual activity. For vaginal heterosexual intercourse, the inhibitory agent could be inserted into the vagina prior to intercourse. For anal intercourse (heterosexual or homosexual), the inhibitory agent could be inserted into the rectum prior to intercourse. For either vaginal or anal intercourse, the inhibitory agents could be incorporated into the lubricant used with the condom. For added protection it is generally preferred that the inhibitory agents be applied before intercourse or other sexual activity and that, if appropriate, a condom be used. For even further protection, the inhibitory agents can be reapplied after completion of the sexual activity; in such cases, a douche or rinse with the inhibitory agent in a liquid carrier solution could be used. Using edible carriers and suitable flavorings, the inhibitory agents could also be used to provide protection during oral sex (heterosexual or homosexual); a mouthwash containing the inhibitory agents could be used afterwards. By incorporating desirable flavorants, scents, fragrances, and colorants, the protective agents could become a "pleasing" or "desirable" component of the sexual activity (i.e., a sex aid or toy) thereby increasing the probability of their use and, therefore, the degree of protection afforded the sexual parties.

One advantage of the present method is that it can be used for protection during a wide variety of sexual activities (vaginal, anal, or oral) by heterosexuals, bisexuals, and homosexuals of either gender. Another advantage of the present method of reducing the transmission of STDs is that this method can be implemented and/or used by either party. Thus, a woman could use the present method to protect herself (as well as her partner) with or without the partner's knowledge of the method being used. Moreover, one partner would not be required to rely on his or her partner's claim of being STD-free or the use of a condom or other barrier devices for protection. Either or both sexual parties could initiate and implement the use of the present method prior to, or after, the sexual encounter. Preferably the method is used before the sexual activity and most preferably both before and after the sexual activity. Although use only after the sexual activity would provide less protection, it would still be desirable to implement this method afterwards if the method was not used prior to the sexual activity for any reason (e.g., in cases of rape). Of course, the sooner this method is initiated after the sexual activity the better. Preferably the method is initiated within one hour, more preferably within 15 minutes, and most preferably almost immediately after the sexual activity. Even after periods greater than these, however, the use of this method as soon as possible after the sexual activity may provide at least some protection (as compared to no treatment).

Still another advantage of the present invention is that, in contrast to other contraceptive or protective methods which rely on a cytotoxic compound (e.g., nonoxynol-9), the inhibitory compounds used in this invention do not significantly affect or inhibit the growth characteristics of the normal vaginal flora or otherwise significantly irritate the vaginal tissue when used at inhibitory, noncytotoxic, or clinical concentrations. Thus, the beneficial components of normal vaginal flora are not disrupted by the use of the present invention. Significant inhibition or modifications of the vaginal flora or other irritations (such as when nonoxynol-9 is used) can lead to increased risks of infections (both STD and non-STD types), unusual discharges, general discomforts, and the like, which, in turn, can lead to a reluctance to use or fully take advantage of the protective method. Such inhibition or modifications of the vaginal flora can also lead to irritation of vaginal tissue and/or lesions which can actually increase the risk of STD transmission and infection. By avoiding or reducing the intensity of these effects, the present method is more likely to be used on a consistent basis. By reducing the number of unprotected sex acts (preferably to zero) and encouraging the use of the methods of this invention both before and after each sex act, the overall degree of protection should be significantly increased. By avoiding or reducing vaginal irritations and especially lesions on the vaginal walls (or rectum lining in the case of anal intercourse), the transmission of STD should be further reduced since transmission of STD-causing organisms is generally easier where damage to the cell walls has occurred. Thus, improvements in ease of use, reduction in side effects, the ability to be initiated by either party, and the ability to be used for different and varied sexual activities give the present invention a significant advantage as a contraceptive and/or as an anti-STD method.

Although not wishing to be limited by theory, it is believed that these inhibitory compounds act, at least in part, by their inhibitory effects on, and related to, carbohydrase (especially hyaluronidase) and/or proteinase and/or by blockage of free sulfhydryl groups on sperm or microbial surfaces. These enzymes (i.e., carbohydrase and proteinase) appear to aid the cellular invasiveness of the STD-causing organisms by, perhaps, (1) causing digesting of substance between the epithelial cells, basal lamina, and the ground substance of the lamina propria and/or (2) assisting target cell penetration and/or (3) inactivation of natural host defenses. It appears that the inhibitory compounds inhibit conception and viral or microbial infections by preventing or significantly disrupting the initial entry, invasion, or deposition of the spermatozoan's DNA into the egg or the initial entry, invasion, or deposition of the infectious organisms'

DNA (or, in some cases, RNA) into the potential host cell, respectively. Blocking or tying up the free sulfhydryl groups on the organisms surface may also impede binding or fusion of the microbial membrane with the host cell plasma membrane and/or penetration into the host cell. These agents may also cause the premature loss of the acrosome from the sperm head, thereby preventing the ability of the sperm to penetrate into the egg. It appears that it is largely the disruption of these entry-related mechanisms—rather than the killing or immobilization of the spermatozoa or infectious organism—which is largely responsible for these compounds' activities.

In a second embodiment, the inhibitory agents of this invention are used to reduce the risk of transmission of STDs, especially HIV/AIDS, to persons who are likely to come in contact with the bodily fluids of STD-infected individuals. This method is not intended to reduce the need and/or use of other protective measures (e.g., protective equipment, proper techniques, and the like), but is rather intended to supplement and increase the protection afforded by these other measures. Of course, this method can also be used where other protective measures are not used for any reason (e.g., emergency situations, unavailability of the protective measures, and the like) or are used improperly. This method is expected to be especially useful for health care providers and laboratory personnel working with samples (e.g., blood, tissue, and the like) from individuals who may be infected with a STD. This method can provide increased protection where such individuals come into physical contact with such bodily fluids. Although the increase in protection afforded to individuals where the contact with bodily fluids is through a break in the skin occurring at the time of the contact (e.g., needle puncture, scalpel cut, and the like where the STD-causing organism may be transmitted directly to the blood stream) may be relatively small, it is better than no added protection.

In this protective method, an effective amount of an inhibitory agent is applied to the skin of an individual which is likely to come into contact with the bodily fluids of another person. For purposes of this invention, "applied to the skin" is intended to cover direct and indirect application to the skin; indirect application is, for example, application to a barrier material (e.g., protective clothing) which then protects the skin. The application of the inhibitory agent is preferably before any contact is likely to occur. More preferably, the application of the inhibitory agent is both before any contact is likely to occur and if, contact occurs or is suspected of occurring, after the actual or suspected contact. Although not the preferred method, where the inhibitory agent was not applied before actual or suspected contact with bodily fluids of another person, the inhibitory agent can be applied only after actual or suspected contact.

The actual method in which the inhibitory agent is applied is not critical so long as an effective amount of inhibitory agent can be delivered to the desired area. Thus, for example, the inhibitory agent can be applied in a lotion, cream, or dry powder formulation to the hands before using latex gloves. Or the inhibitory agent could be applied to the interior and/or exterior of latex gloves. Or the inhibitory agent could be incorporated into latex gloves or other protective clothing or equipment as a coating or as a component thereof. Or the inhibitory agent could be applied as a protective cream layer over skin likely to be exposed. Or the inhibitory agent can be included as an aqueous formulation to be delivered via eye-wash or full-body wash stations located in areas where contact is likely to occur (i.e., emergency rooms, laboratories, and the like). Or the inhibitory agents could be included in materials used to clean up biological materials and wastes (i.e., from surgery or other invasive or noninvasive procedures) so that if later contact does occur with individuals handling the material (e.g., support staff, cleaning staff, waste disposal personnel, and the like), transmission of the STD-causing organisms is less likely to occur. Of course, many other means of delivery of the inhibitory agent can be used.

Suitable inhibitory agents include phosphorylated hesperidins, sulfonated hesperidins, polystyrene sulfonates, substituted benzenesulfonic acid formaldehyde co-polymers, and $H_2SO_4$-modified mandelic acids. Preferably these inhibitory agents are included in an inert carrier and are applied before contact with the bodily fluids of another person is likely to occur. During long procedures, it may be preferable to reapply the inhibitory agents several times during the procedure. If actual contact with bodily fluids does occur (or if only suspected of occurring), the inhibitory agents (in the same or different carriers) are preferably reapplied immediately and further medical attention sought.

Generally aqueous-based carriers are preferred. The carrier can contain other ingredients if desired; generally the same optional ingredients as used in the sexual activity applications can be included. Moreover, generally the effective amounts of inhibitory agents, types of inhibitory agents, methods for preparing the inhibitory agents, carriers, optional ingredients, and the like for the health-care provider applications are the same (or at least similar taking into account the differences in applications) as for those used in the sexual activity applications. Thus, it is not necessary to repeat these details specifically in regard to the health-care provider applications and uses.

The phosphorylated hesperidins can be prepared by mixing pyridine and hesperidin with phosphorous oxychloride as described by Beiler and Martin, *J. Biol. Chem.* 174 31–35 (1948), which is hereby incorporated by reference. Once the reaction mixture (pyridine, hesperidin, and phosphorous oxychloride) has cooled, the precipitate is collected and dissolved in water. The solution is preferably filtered and reprecipitated with ethanol two times. The final precipitate is dissolved in a minimal amount of water and dried under vacuum. The phosphorylated hesperidin prepared by the procedure appears to be a mixture of penta- and tetra-phosphates of hesperidin.

The sulfonated hesperidins can be prepared by mixing hesperidin and sulfuric acid as also described by Beiler and Martin, *J. Biol. Chem.* 174 31–35 (1948). The reaction mixture (hesperidin and $H_2SO_4$) is added to ethanol, neutralized with saturated NaOH, and then filtered to remove the precipitated $Na_2SO_4$. The filtrate and washing solutions are made alkaline with NaOH and precipitated in ethanol. The final product is obtained by dissolution in water, reprecipitation in ethanol, and vacuum evaporation. The sulfonated hesperidin prepared by the procedure appears to be a mixture of mono- and di-sulfonates of hesperidin.

The phosphorylated hesperidins and sulfonated hesperidins have both contraceptive and anti-STD activities without significant cytotoxic effects. These compounds inhibit a number of enzymes, including sperm hyaluronidase, serine proteinase acrosin, and β-glucuronidase; β-N-acetylglucosaminidase and β-galactosidase are not inhibited.

Oral or intraperitoneal administration of phosphorylated hesperidin is reported to partially or completely prevent fertilization in mice, rats, and humans. Vaginally placed phosphorylated hesperidin is also effective as a contraceptive. Treatment of rabbit spermatozoa with about 10 mg/ml of phosphorylated hesperidin prior to vaginal insemination decreased fertilization rates from about 100 percent to about 17.5 percent. Higher contraceptive activity was found when phosphorylated hesperidin was mixed with jelly and placed vaginally before insemination. One study found that, at 10 mg/ml (total dose of 15 mg), implantation/fetal development was depressed by about 78 percent; another study found that the same levels of phosphorylated hesperidin placed vaginally in rabbits before artificial insemination reduced fertilization rates from about 94 percent to about 0.5 percent. Phosphorylated hesperidin appears to be an even more effective contraceptive than nonoxynol-9.

Using a cell-free virus inactivation assay, phosphorylated hesperidin (0.05 and 1.0 percent in water) produced 1.5 and 2.2 log reductions, respectively, in the infectivity of human immunodeficiency virus (HIV-1, RF strain). For the cell-free virus inactivation assay, HIV is added to the test agent in water and incubated for about 2 minutes. After removal of the test agent by dilution, the treated virus is added to target cells and incubated for 7 days. The observed inhibition in the cell-free virus inactivation assay could have resulted from either he phosphorylated hesperidin treatment and/or the decrease in pH during the test.

Using a viral-binding inhibition assay, phosphorylated hesperidin in water was found to be 100 percent effective in preventing HIV infection at a level of about 0.05 percent (about 500 $\mu$g/ml), about 85 percent effective at a level of about 0.005 percent (about 50 $\mu$g/ml), and about 70 percent effective at a level of about 0.001 percent (about 10 $\mu$g/ml). Even at a level of about 0.0001 percent (about 1 $\mu$g/ml), phosphorylated hesperidin reduced HIV infectivity by about 36 percent. Using the viral-binding inhibition assay, sulfonated hesperidin in water inhibited HIV infectivity by 85 and 48 percent at concentrations of 0.005 percent (about 50 $\mu$g/ml) and 0.001 percent (about 10 $\mu$g/ml), respectively. (In the viral-binding inhibition assay, the agent is mixed with virus and target cells; syncytium formation among target cells is determined after incubation.) No toxicity was observed towards the host cells at the concentration ranges used for the phosphorylated and sulfonated hesperidins.

Phosphorylated hesperidin and sulfonated hesperidin also have significant anti-HSV activity. Viral infectivity was measured by co-culturing herpes simplex virus (HSV) with Vero (African green monkey kidney) cells in phosphate-buffered solutions. Greater than 99 percent HSV inhibition occurred at concentrations of phosphorylated hesperidin of 0.001 percent (10 $\mu$g/ml); HSV inhibitions of 88 percent and 35 percent resulted with phosphorylated hesperidin concentrations of 0.0001 percent (about 1 $\mu$g/ml) and 0.00001 percent (about 0.1 $\mu$g/ml), respectively. Sulfonated hesperidin decreases HSV infectivity by 13 percent at a level of 0.0001 percent, by 63 percent at a level of 0.001 percent, and by virtually 100 percent at a level of 0.01 percent. Both phosphorylated hesperidin and sulfonated hesperidin are expected to inhibit other organisms (both STD-causing and non-STD-causing microbes).

Both phosphorylated hesperidin and sulfonated hesperidin are expected to be safe for use with humans. Both oral and intravenous dosages (up to 20 g/day for 10 days) of phosphorylated hesperidin did not produce any toxic manifestation or allergic reactions in humans. Moreover, the parent compound hesperidin as well as other hesperidin derivatives also appear to be safe for human use.

The polystyrene sulfonates suitable for use in this invention are available commercially, although they are preferably further purified before use. For example, a polystyrene sulfonate having a molecular weight of about 500,000 to 700,000 is available from National Starch (Bridgeport, N.J.) under the tradename Versa-TL 502. Generally, polystyrene sulfonate intended for industrial use (e.g., as an antistatic or emulsifying agent) may contain low levels of dichloroethane (ranging from about 50 to 700 ppm). For use in the present method, it is preferable that the dichloroethane levels are reduced to less than about 50 ppm and more preferably to less than about 10 ppm using suitable purification techniques.

Sulfonated polystyrene polymers also have both contraceptive and anti-STD activities without significant cytotoxic effects. Polystyrene sulfonates inhibit a number of enzymes, including sperm hyaluronidase. The inhibition of hyaluronidase is irreversible with an $IC_{50}$ (level that inhibits activity by 50 percent) of about 5.7 $\mu$g/ml (at 0.1 mg/ml, inhibition is about 96 percent). Polystyrene sulfonate has been shown to be more effective than nonoxynol-9 as a vaginal contraceptive in rabbits. When incorporated into a gel formulation, polystyrene sulfonate also appears to have extended contraceptive activity. The same contraceptive effect has been observed even when mating has been delayed up to eight hours after vaginal placement of the material. Moreover, the same contraceptive effect has been observed with multiple matings (one upon placement and another 2–4 hours afterwards).

Using a viral-binding inhibition assay, polystyrene sulfonate (molecular weight of about 500,000 g/mole) inhibits the HIV virus with an $IC_{50}$ of bout 2.8 $\mu$g/ml. A concentration of 50 $\mu$g/ml was found to completely inhibit HIV. Polystyrene sulfonate inhibits HSV with an $IC_{50}$ of about 0.007 $\mu$g/ml. Three-log (99.9 percent) and four-log (99.99 percent) reductions for HSV were calculated to be about 3.1 $\mu$g/ml and about 23 $\mu$g/ml, respectively. In a multiplication (replication) assay, polystyrene sulfonate was found to be an effective anti-gonococcal agent with an $IC_{50}$ of about 3 $\mu$g/ml; three-log (99.9 percent) and four-log (99.99 percent) reductions were calculated at about 23 $\mu$g/ml and 35 $\mu$g/ml, respectively. No toxicity was observed towards the host cells at the concentration ranges used. Polystyrene sulfonate does not appear to significantly effect normal vaginal flora.

The substituted benzenesulfonic acid formaldehyde co-polymers are prepared by the copolymerization of substituted benzenesulfonic acids and formaldehyde under basic conditions using conventional polymerization techniques. One such synthetic method is described by Rogers and Spensley, *Biochim. Biophys. Acta.* 13 293–294 (1954), which is hereby incorporated by reference. Generally the synthetic method described in Example 3 below is preferred as it produces a product with increased inhibitory effects at higher yield as compared to the Rogers and Spensley method. Examples of suitable substituted benzenesulfonic acids include hydroquinone sulfonic acid, catecholsulfonic acid, phenolsulfonic acid, and the like. The preferred substituted benzenesulfonic acid is hydroquinone sulfonic acid; thus the preferred substituted benzenesulfonic acid formaldehyde co-polymer is hydroquinone sulfonic acid formaldehyde co-polymer. A preferred hydroquinone sulfonic acid formaldehyde co-polymer ($PS_{53}$) is prepared by mixing hydroquinone sulfonic acid, formaldehyde, and sodium hydroxide in water and refluxing at about 65 to 70° C. for about 5 hours. Preferably the reaction mixture is then neutralized with HCl (generally about 1N), after which the product is dialyzed exhaustively. The nondialyzable material is then lyophilized to obtain the $PS_{53}$ product.

The substituted benzenesulfonic acid formaldehyde co-polymers—and especially $PS_{53}$—also have both contraceptive and anti-STD activities without significant cytotoxic effects. $PS_{53}$ (and related substituted benzenesulfonic acid formaldehyde co-polymers) inhibit a number of enzymes, including sperm hyaluronidase, serine proteinase acrosin, and β-glucuronidase; β-N-acetylglucosaminidase and β-galactosidase are not inhibited. The inhibition of hyaluronidase is irreversible. $PS_{53}$ is also very effective in blocking free sulfhydryl groups on human sperm surfaces and probably on microbial surfaces.

Fertilization was completely inhibited when $PS_3$ was added to rabbit spermatozoa at an effective dosage of about 0.5 to 2.0 mg/ml before vaginal insemination. $PS_{53}$ also prevented conception when placed vaginally (about 10 to 14 mg/ml in a jelly lubricant for a total dosage of about 15 to 21 mg) prior to insemination. Even lower dosages (about 3.75 mg total) also significantly reduce the fertilization rate. Thus, it appears that a dose of about 3.75 mg will prevent conception to a significant degree and a dose of about 15–20 mg will essentially prevent conception. Indeed, $PS_{53}$ appears to be an even more effective contraceptive than nonoxynol-9.

Using a viral-binding inhibition assay, $PS_{53}$ (dialyzed using a membrane with a molecular weight cut-off of 6,000 to 8,000) in saline was found to be 100 percent effective in preventing HIV infection at a level of about 0.01 percent (about 100 μg/ml) and about 97 percent effective at a level of about 0.005 percent (about 50 μg/ml). Even at a concentration of only about 0.0001 percent (about 1 μg/ml), infectivity was reduced by about 44 percent. A similar saline solution, prepared with $PS_{53}$ dialyzed using a membrane with a molecular weight cut-off of 12,000 to 14,000, inhibited HIV by about 80 percent at a level of 0.01 percent, about 60 percent at a level of 0.005 percent, and about 2 percent at a level of 0.0001 percent. These results suggest that the molecular weight fraction between these two cut-off ranges may have particularly strong anti-HIV activity. Little or no toxicity was observed towards the host cells at the concentration ranges used.

$PS_{53}$ also has significant anti-HSV activity. Viral infectivity was measured after co-culturing herpes simplex virus (HSV) with Vero (African green monkey kidney) cells in phosphate-buffered solutions as described above. $PS_{53}$ had an $IC_{50}$ of less than 0.00001 percent (0.1 μg/ml); $PS_{53}$ had an $IC_{100}$ of less than 0.001 percent (10 μg/ml). $PS_{53}$ was noncytotoxic to the cultured cells at the highest levels (0.05 percent; 500 μg/ml) evaluated. $PS_{53}$ is expected to be safe for use with humans. An $LD_{50}$ of about 1.25 g/kg has been determined in mice. Moreover, mice fed 400 mg/kg per day for 21 days did not show toxic symptoms.

The $H_2SO_4$-modified mandelic acid is prepared by treating mandelic acid with sulfuric acid as described in Example 4 below. Although the structure of the $H_2SO_4$-modified mandelic acid had not been fully determined as of the original filing date, preliminary elemental analysis confirm the absence of sulfur. Thus, it appeared that sulfonation of the mandelic acid does not occur to any appreciable degree. Although not wishing to be limited by theory, we thought that the $H_2SO4$-modified mandelic acid consisted of five components (molecular weights of 312, 326 (two forms), and 340 (two forms)) with the main component having a molecular weight of 312 and an empirical formula of $C_{18}H_{16}O_5$. Again not wishing to limited by theory, we thought that this major component was likely to be a poly-aromatic carboxylic acid derivative formed, at least in part, by acid catalyzed electrophilic substitution type mechanism. More detailed structural studies have now been completed. Still not wishing to be limited by theory, it now appears that the main active component in the $H_2SO_4$-modified mandelic acid is a dimeric form of mandelic acid (i.e., 2,2'-diphenyl-2,2'-oxy-di-acetic acid) of the general formula:

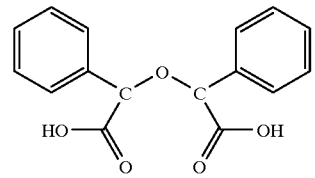

Regardless of the structure, the $H_2SO_4$-modified mandelic acid—that is, the reaction product of sulfuric acid and mandelic acid—has very high contraceptive and anti-microbial activities. Sulfuric acid treated substituted mandelic acids can also be used in the practice of this invention. For example, dimeric forms of substituted mandelic acids of the general formula:

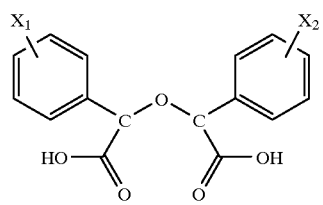

where $X_1$ and $X_2$ are, independently, —OH, —OR, or halides and R can be alkyl or substituted alkyl radicals having from 1 to 6 carbon atoms or aryl or substituted aryl radicals, may also be used in the present invention.

This reaction product has a strong inhibitory effect on hyaluronidase with an $IC_{50}$ value of 8.4 μg/ml. It is a potent stimulus of sperm acrosomal loss: about 70 percent maximal acrosomal loss is induced at 0.5 μg/ml. This reaction product is also a highly effective contraceptive: nearly complete inhibition of conception was observed when rabbit sperm was treated with about 5 mg/ml of the reaction product prior to artificial insemination.

The $H_2SO_4$-modified mandelic acid is also a potent anti-HIV and anti-HSV agent. HSV was completely inhibited in culture when treated with 10 μg/ml of the reaction product. The reaction product is viricidal towards HIV, as measured by a cell-free virus inactivation assay, with nearly complete kill (about 99 percent) of the virus in culture with exposures as low as 10 μg/ml. The reaction product is also effective as an anti-gonococcal agent with complete inhibition of gonococcal growth in culture when treated at 100 μg/ml of the reaction product.

In spite of its viricidal activity, the $H_2SO_4$-modified mandelic acid shows no cytotoxic activity towards spermatozoa. Exposure to concentrations as high as 20 mg/ml did not result in the loss of sperm motility. Moreover, there is no apparent adverse effects of this reaction product on normal vaginal flora. Lactobacillus growth in culture was not affected by exposure to the reaction product at concentrations as high as 5 mg/ml.

EXAMPLES

Example 1

This example illustrates the preparation of a phosphorylated hesperidin. Hesperidin (97%; 9.25 g; 15.15 mmole)

was added to 100 ml pyridine (99%) with stirring under ambient conditions over a 30 minute period. A dark brown solution was obtained. Phosphorous oxychloride ($POCl_3$; 99%; 25 ml) was added slowly to the reaction mixture so that the temperature remained between about 30 to 50° C. After addition of the first 5 ml of $POCl_3$, a precipitate was formed which made stirring difficult. The entire amount of $POCl_3$ was added over a 50 minute period and the reaction continued for an additional 30 minutes. The reaction mixture (very dark reddish brown) was cooled with an ice bath and then 50 ml water was slowly added. The reaction mixture was allowed to stand overnight at about 4° C. The precipitate was collected by centrifugation (1000 G for 6 minutes). The supernate (dark brown; about 50 ml) was collected; the "sticky" precipitate was discarded. The supernate was slowly added to absolute ethanol (about 160 ml) with stirring. The resultant precipitate was filtered under vacuum and washed twice with cold ethanol (20 ml). The crude product is a brown-yellow solid. The crude product was dissolved in water (10 ml); undissolved material was removed by centrifugation (1000 G for 6 minutes). The supernate was then added to 50 ml cold absolute ethanol with stirring. After filtering with vacuum, the filtered material was washed twice with absolute ethanol (about 20 ml). The filtered material was then vacuum dried to yield about 4 g (about 27 percent assuming an equal mixture of tetra- and penta-phosphates and $M_r$ of 930.6 and 1010.6, respectively) of the brown-yellow solid phosphorylated hesperidin. This sample (or one similarly prepared) was used throughout the Examples.

The phosphorylated hesperidin was highly water soluble at pHs ranging from about 2 to 9; in all cases, the solubility was greater than 180 mg/ml. The ultraviolet spectra in water gave a broad absorbance at 256 nm (absorbance of about 0.330 at 20 µg/ml). High performance liquid chromatography was performed with a stainless steel column (30×0.39 cm) packed with RP-18 Bondclone (10 µm; Phenomenex (Torrance, Calif.)). Elution material was detected with a LDC/Milton Roy spectromonitor D variable wavelength and Refractomonitor III detectors. Elution using a mobile phase of water/acetonitrile/THF/acetic acid (80:16:3:1) and a flowrate of 1 ml/min resulted in two peaks at retention times of 2.54 minutes (about 70 percent of eluted material) and 3.49 minutes (about 30 percent of eluted material). Hesperidin was not observed. Phosphorylated hesperidin was scanned for fluorescence with a Perkin Elmer LS-5B luminescence spectrometer. At a concentration of 1 µg/ml in water and a pH of 10.8 (adjusted with NaOH), maximum fluorescence was obtained at excitation and emission wavelengths of 260 nm and 520 nm, respectively. Under these conditions, detection of concentrations as low as about $10^{-12}$ g/ml is possible.

Example 2

This example illustrates the preparation of a sulfonated hesperidin. Hesperidin (97%; 4.0 g; 6.6 mmoles) was added over a 60 minute period to sulfuric acid (66° baume; 10 ml) under ambient conditions with stirring. Stirring was continued for an additional 30 minutes. The reaction mixture was then added to about 50 ml absolute ethanol. After cooling with an ice bath, the pH was adjusted to about 7 with aqueous NaOH (saturated). The resulting precipitate was vacuum filtered and then washed twice with absolute ethanol (10 ml). The ethanol washes were combined with the filtrate. The white residue was discarded.

After adjusting the pH of the filtrate to about 9–10 with saturated NaOH, about 100 ml absolute ethanol was added to precipitate the product. After standing at about 4° C. overnight, the precipitate was collected by filtration and washed twice with absolute ethanol (10 ml). After drying under vacuum, about 4.0 g (about 86 percent assuming an $M_r$ of 705) of the yellow-brown solid sulfonated hesperidin was obtained. This sample (or one similarly prepared) was used throughout the Examples.

The sulfonated hesperidin was highly water soluble at pHs ranging from about 2 to 9; in all cases, the solubility was greater than 200 mg/ml. The ultraviolet spectrum in water gave a broad absorbance peak with a maximum at 288 nm. High performance liquid chromatography (conditions and equipment as outlined in Example 1) gave only a single peak at room temperature (with a shoulder which could not be resolved by varying the conditions); hesperidin was not observed.

Example 3

This example illustrate the preparation of $PS_{53}$. Water (300 ml; double distilled) and NaOH (31.5 g; 0.79 moles; Fisher ACS reagent) were placed in a 1 liter resin kettle equipped with a mechanical stirrer, vacuum tight stirrer bearing, and a reflux condenser. Hydroquinone sulfonic acid (150 g; 0.66 moles; Sigma photographic grade) was then added followed by formaldehyde (131 ml; 1.65 moles; Fisher ACS reagent). After addition of the hydroquinone sulfonic acid the reaction mixture darken significantly. The reaction mixture was then heated to reflux and maintained under reflux conditions for two hours. (During reflux, the external heat source was maintained below about 130° C.) Additional formaldehyde (131 ml; 1.65 moles) was then added over about 30 minutes and reflux continued for an additional three hours.

The reaction mixture (pH about 9.5) was cooled to less than about 80° C. Sulfuric acid (30% v/v; Fisher ACS reagent) was slowly added with stirring to a pH of about 3.0. After modifying the apparatus for vacuum distillation, the pressure was reduced to about 50–70 mm Hg and vacuum distillation was begun. The external heat source was kept below about 120° C. to avoid excessive charring of the product. Distillation was continued with stirring until a thick tar was obtained. Distillation continued without stirring until an extremely thick tar (and some solid on the reactor walls) was obtained. The internal temperature during the distillation should not exceed about 70° C. The total distillation time was generally about 3 hours.

The reaction mixture was then cooled to about 40° C. and double distilled water (about 500 ml) added. The reaction mixture stood for about 30 minutes during which time the polymer tar softens. The reaction mixture was then stirred for about 1–2 hours to dissolve the polymer tar. The pH was adjusted to about 7.0 using aqueous NaOH (20% w/v). The resulting viscous, dark solution was filtered. The filtrate was then dialyzed to remove low molecular weight oligomers and salts using a Spectrum hollow fiber bundle (molecular weight cutoff of about 13,000) against distilled water. Dialysis continued until the dialysate was only faintly colored. The solid polymer product (115 g; about 73 percent yield) was isolated by freeze drying. This sample (or one similarly prepared) was used throughout the Examples.

The $PS_{53}$ product was a water soluble, dark brown-tan amorphous solid. IR (KBr pellet): 3340 $cm^{-1}$ (OH); 2938 $cm^{-1}$ (Ar—H); 1650 $cm^{-1}$ (C=O, C=C); 1196 $cm^{-1}$ (asymm. $SO_2$); 1044 $cm^{-1}$ (symm. $SO_2$). UV ($H_2O$): 205, 266 (broad), 310 (broad) nm. C-13 NMR (100 MHZ, $D_2O$, 300° K.): 150.7 ppm (aromatic C); 128.7 (aromatic C); 122 ppm (aromatic C); 57.7 ppm ($CH_2$); 51.0 ppm ($CH_2$). Although all C-13 NMR peaks tended to be extremely broad due to the high molecular weight of the polymer, it appears that the ratio of aromatic to methylene carbons is about 3:1. This ratio suggests that the polymer is not linear (ratio should be about 6:1) but rather branched on most or all available sites to give a crosslinked polymer. The dialyzed product had a symmetrical molecular weight distribution (HPCL GPC-SEC chromatography analysis) centered around about 7,900 to 8,000.

The just described preparation of $PS_{53}$ represents a significant improvement over the published method (Rogers and Spensley, *Biochim. Biophys. Acta.* 13 293–294 (1954)). For example, the just-described method generally provides a yield of about 70 percent or higher as compared to a yield of about 11 percent for the published method. Moreover, the just-described method provides a product with a molecular weight of about 8000 as compared with a value of about 3000 for the published method. In addition, the polymer obtained by the just-described method appears to be a more effective inhibitor of sperm hyaluronidase that the material produced by the published method.

Example 4

This example illustrates the preparation of $H_2SO_4$-modified mandelic acid. D,L-mandelic acid (9.0 g) was added to concentrated $H_2SO_4$ (9.0 ml) with constant stirring over a 20 minute period. During the addition, the temperature was allowed to rise from ambient to about 55° C. The reaction mixture was heated to 80° C. for an additional 40 minutes at which time the reaction was terminated by the addition of 130 ml ice cold ethanol (absolute). Saturated sodium hydroxide was added with stirring to a pH of 3 to 4. The resulting suspension was vacuum-filtered and washed with about 60 ml cold ethanol (absolute). Saturated sodium hydroxide was added to the combined filtrates until a pH of about 12 to 13 was obtained. The resulting precipitate (yellow to orange-yellow) was collected using vacuum filtration. After washing with about 50 ml ethanol (absolute), the precipitate was air dried.

The air-dried precipitate was suspended in water (about 1:3 by weight) and the pH was adjusted to about 12–13 with sodium hydroxide. After vacuum filtration, the filtrate was added to about 100 ml ethanol (absolute) at room temperature. The resulting precipitate product, as the sodium salt, was collected by filtration and dried at 75° C. The final product (yield about 10.2 g) was a light burnt orange to light pink powder with a water solubility of about 350 mg/ml and a melting point of about 214–218° C. (decomp.). The following elemental analysis was obtained: Carbon—67.7±0.9 percent; hydrogen—4.3±0.2 percent; sulfur—zero; and oxygen—28.0±1.1 percent. The "free acid" form contained 6.4 μeq of titratable acid groups per mg of solid based on titration with sodium hydroxide. Liquid chromatography/mass spectroscopy analysis indicated five components with molecular weights as follows: about 312, 326 (two forms), and 340 (two forms) in the approximate abundance ratios of about 5.7 to 4.5 to 3.5 to 1.1 to 1.0, respectively. The major component has a molecular weight of 312 and, based on the elemental analysis, a empirical formula of $C_{18}H_{16}O_5$. Although work on the structure is ongoing, it is likely to be a poly-aromatic carboxylic acid derivative formed at least in part by an acid catalyzed electrophilic substitution reaction.

The above method can be modified such that the reaction is terminated and the reaction product precipitated by the addition of water (about 150 ml) at room temperature rather than the addition of absolute alcohol as described above. With this modified procedure, the free acid form of the product is isolated by vacuum filtration and then treated with saturated sodium hydroxide to form the sodium salt. Although the above-described procedure appears to give a purer product (i.e., lighter in color), the biological properties of the two materials are very similar.

Example 5

This example illustrates an improved method for the preparation of $H_2SO_4$-modified mandelic acid wherein the mandelic acid is reacted with sulfuric acid at low temperatures (generally about 0° to about 10° C., and preferably about 0° to about 5° C.). Concentrated sulfuric acid (40 ml) was added dropwise to a $CH_2Cl_2$ (150 ml) solution containing mandelic acid (20 gm, 0.13 mol) over 5 min at 0° C. The reaction mixture was stirred at 0° C. for 30 min., lowly warmed to room temperature, and then stirred at room temperature for 3 hours. $CH_2Cl_2$ was decanted and the remaining residue was poured into 300 ml of ice-water in a beaker to afford a white precipitate. The white precipitate was ground using a mortar and pestle and was washed with water (300 ml). The white precipitate was vacuum filtered and air dried. The precipitate was column chromatographed over Amberchrom CG-161 md using isopropyl alcohol and water (2:1) as eluent. Yield: 95%. Color: off-white. Physical property: hygroscopic. Molecular formula: $C_{16}H_{14}O_5$. Molecular weight: 286.28. Elemental analysis: Calculated: C: 67.13; H: 4.93; Found: C: 67.20; H: 4.84. The structure was confirmed as the dimer of mandelic acid.

In order to prepare the disodium salt, sodium hydroxide (NaOH, 6.68 gm, 0.0824 mol) was added to 11.8 gm of the previous product in 100 ml water under stirring to obtain a clear solution. The solution was filtered and the solvent removed in vacuo to afford an off-white solid in quantitative yield. Color: off-white. Physical property: water soluble.

Example 6

This example illustrates the anti-HIV activity of the inhibitory agents of this invention using a viral binding inhibition assay. Cultures of MT2 cells (plated in 96-well cell culture plates at about 10,000 cells per well) were grown in a RPMI 1640 medium (Gibco, cat. no. 320-1867AG) which was supplemented with 10 percent fetal bovine serum, 100 I.U./ml penicillin, 100 μg/ml streptomycin, 20 μg/ml gentamicin, and 25 mM HEPES. Test compounds were prepared as described in Examples 1–5. Polystyrene sulfonate having a molecular weight of about 500,000 to 700,000 was obtained from National Starch (Bridgeport, N.J.) under the tradename Versa-TL 502; purification to less than about 50 ppm dichloroethane was carried out by National Starch; this material was used throughout the Examples.

Serial dilutions of the test compounds (ranging from 0.1 μg/ml to 1.0 mg/ml) were added to HIV-1 virus such that 50 μl inoculum produced between 70 to 100 syncytia per well in untreated wells containing MT2 cells. The HIV-1 used was strain III, propagated in, and harvested from, a T4-lymphobastoid cell line. Each serial dilution of the test compound with virus was placed in each of three wells containing MT2 cells. The test compound alone was added to a fourth well containing MT2 cells to test for possible cytotoxicity. Triplicate virus control samples (no added test compounds but containing the equivalent amounts of the RPMI medium) were also included.

The resulting cultures were incubated at 37° C. (5 percent $CO_2$ levels) for 48–72 hours. The cultures were then scored microscopically for syncytia formation. If no activity was observed at the highest concentration for a given test compound, the test compound was considered to be inactive. If 90 to 100 percent inhibition was observed at the lowest concentration, the tests were repeated with lower concentrations. Data are expressed as percent of a control value (no added test agent) viral titer and plotted as a function of concentration of the test agent. $IC_{50}$ values (concentration of agent causing 50 percent inhibition) were calculated from the plots of concentration versus viral titer using curve-fitting software. Similar tests were run to determine the lowest concentration at which complete inhibition occurs.

The results are reported in the following table.

| Agent | $IC_{50}$ | Complete Inhibition |
|---|---|---|
| Control | inactive | — |
| Phosphorylated Hesperidin | 2.8 µg/ml | 500 µg/ml |
| Sulfonated Hesperidin | 10.8 µg/ml | 100 µg/ml |
| $PS_{53}$ | 1.8 µg/ml | 10 µg/ml |
| Polystyrene Sulfonate | 2.8 µg/ml | 50 µg/ml |
| $H_2SO_4$-modified Mandelic Acid | 0.3 µg/ml | 5 µg/ml |

The various inhibitory agents were not cytotoxic towards the MT2 cells at these levels. Nonoxynol-9 did show cytotoxic effects. The results for the $H_2SO_4$-modified mandelic acid from Examples 4 and 5 were essentially identical.

Example 7

This example illustrates the anti-HSV activity of the inhibitory agents of this invention. The test agent was serially diluted (0.1 µg/ml to 500 µg/ml) in phosphate-buffered saline (PBS). Each dilution was mixed with HSV (type 2, strain 333). Samples (1 ml) of each mixture were plated in triplicate on washed and drained monolayers of Vero (African green monkey kidney) cells on the bottom of 25 cm³ flasks. The initial titer in each culture was determined as plaque forming units per milliliter using control cultures with no added test agents. Flasks were incubated at 37° C. for 2 hours and the medium (containing virus and test agent) removed. After washing the cells with PBS, the cells were cultured in supplemented medium 199 (Sigma Chem., cat. no. M9163) for 3 days. After culturing, the cells were stained with Giemsa and the number of viral plaques was determined by phase contrast microscopy. After correcting for dilutions, the viral titer was estimated from the number of plaques. Data were also expressed as the percentage of plaques relative to the control samples (not exposed to test agents). Data obtained with the highest concentration of test agent were compared with the control samples; compounds which showed no activity at this highest concentration were considered to be inactive. If 90 to 100 percent inhibition was observed at the lowest concentration, tests were repeated at still lower concentration levels. The concentration of test agent that was required to reduce the viral titer by 50 percent ($IC_{50}$) was estimated with curve-fitting software from plots of plaque-forming units per milliliter against the concentration of test agent. Three-log (99.9 percent) inhibition and four-log (99.99 percent) inhibition were also calculated from this data.

The results are reported in the following table.

| | | Inhibition | |
|---|---|---|---|
| Agent | $IC_{50}$ | 3-Log | 4-Log |
| Control | inactive | — | — |
| Phosphorylated Hesperidin | 0.2 µg/ml | 365 µg/ml | 4.2 mg/ml |
| Sulfonated Hesperidin | 6.4 µg/ml | 3.4 mg/ml | 27.5 mg/ml |
| $PS_{53}$ | 0.04 µg/ml | 2.8 µg/ml | 9.2 µg/ml |
| Polystyrene Sulfonate | 0.007 µg/ml | 3.1 µg/ml | 23 µg/ml |
| $H_2SO_4$-modified Mandelic Acid | 0.2 µg/ml | 6.8 µg/ml | 10 µg/ml |

Example 8

This example illustrates the hyaluronidase inhibition properties of the inhibitory agents of the present invention. Hyaluronidase activity was quantitatively determined by measuring the extent of hyaluronic acid hydrolysis (i.e., the concentration of N-acetylglucosamine-reactive material formed from enzyme activity). Reaction mixtures (0.25 ml) containing the following were prepared: test compound (variable concentration); 0.1 M sodium acetate; 0.15 M sodium chloride; pH adjusted to 5.5; 7.2 units sheep testicular hyaluronidase (Sigma, Type III; H-2251) contained in an acetate buffer; 0.3 mg/ml hyaluronic acid (Sigma, from bovine vitreous humor; H-7630). The enzyme was preincubated with the test agent (1 mg/ml for screening purposes) for 10 minutes before starting the reaction by the addition of hyaluronic acid. The enzyme reaction was determined using the method of Aronson and Davidson (*J. Biol. Chem.* 241 437–440 (1967)). The reaction mixture was incubated for 30 minutes at room temperature. The reaction product was determined colorimetrically with p-dimethylaminobenzaldehyde (Reissig et al., *J. Biol. Chem.* 217 959–966 (1965)) by measuring the absorbance at 545 nm.

Compounds which showed no inhibition at the screening concentration of 1 mg/ml were considered to be inactive. If the test agent showed inhibition at the screening concentration, a dose-response curve was generated from which $IC_{50}$ values could be determined using curve-fitting software. The following results were obtained.

| Agent | $IC_{50}$ | Inhibition |
|---|---|---|
| Control | inactive | — |
| Nonoxynol-9 | inactive | — |
| Phosphorylated Hesperidin | 499 µg/ml | 90% at 1 mg/ml |
| Sulfonated Hesperidin | 150 µg/ml | 89% at 1 mg/ml |
| $PS_{53}$ | 20 µg/ml | 100% at 1 mg/ml |
| Polystyrene Sulfonate | 5.7 µg/ml | 96% at 100 µg/ml |
| $H_2SO_4$-modified Mandelic Acid | 8.4 µg/ml | 100% at 1 mg/ml |

The reversibility of the hyaluronidase was determined by evaluating enzyme activity at different levels of enzyme (Ackermann and Potter, *Proc. Soc. Exp. Biol. Med.* 72 1–9 (1949)). Hyaluronidase inhibition was irreversible for sulfonated hesperidin, $PS_{53}$, $H_2SO_4$-modified mandelic acid, and polystyrene sulfonate. Hyaluronidase inhibition by phosphorylated hesperidin appears to be reversible.

Example 9

This example illustrates the effect of the inhibitory agents of this invention on the normal vaginal flora. *Lactobacillus gasseri*, which is found in normal vaginal flora, was obtained from the American Type Culture Collection (Rockville, Md.) and cultured under anaerobic conditions at 37° C. in the presence of the desired test agents. Control samples without added test agents were also run. Samples were collected at twenty minute intervals starting at 120 minutes after the start of incubation through 240 minutes. The absorbance at 550 nm was used to estimate the cell density and inhibitory effects. Nonoxynol-9 was also evaluated for comparison purposes.

Sulfonated hesperidin, phosphorylated hesperidin, and $H_2SO_4$-modified mandelic acid at 5 mg/ml did not have any effect on the growth of *Lactobacillus gasseri*. $PS_{53}$ had some weak inhibitory effect on the growth of this bacteria; about 45 percent inhibition was observed at 5 mg/ml. Polystyrene sulfonate had no inhibitory effect; numerically, about 7 percent inhibition, which was not considered significant, was observed at 5 mg/ml. Nonoxynol-9 was highly inhibitory to this bacteria; about 60 percent inhibition was observed at 0.5 mg/ml. Sulfonated hesperidin, phosphorylated hesperidin, polystyrene sulfonate, and $H_2SO_4$-modified mandelic acid are expected to have no significant effect on normal vaginal flora when used at clinical levels in the vagina. $PS_{53}$ is expected to have only mild effects on the normal vaginal flora when used at clinical levels.

Example 10

This example illustrates the inhibitory effect for several of the inhibitory agents of this invention on *Neisseria gonorrhea* using a bacterial multiplication assay. *Neisseria gonorrhea* isolated from local uncomplicated cases of gonorrhea was verified by Gram stain, oxidase reactivity, and sugar fermentation. The titer of log-phase cultures was adjusted by dilution in GC broth to about $10^8$ colony forming units per milliliter. Samples were diluted with broth containing no additives (control) and serial dilutions of the test agents (1000 $\mu$g/ml to 0.1 $\mu$g/ml). The resulting cultures were incubated at 37° C. for 4 hours. Five serial dilutions were made with GC broth; each dilution was inoculated onto GC agar plates. The inoculated plates were incubated overnight at 37° C. and the resultant gonococcal colonies were counted using bright-field microscopy.

Neither sulfonated nor phosphorylated hesperidins had any effect on gonococcal multiplication up to a level of 1 mg/ml. Polystyrene sulfonate was an effective gonococcal agent with an $IC_{50}$ of about 3 $\mu$g/ml. The three-log (99.9 percent) and four-log (99.99 percent) reductions for polystyrene sulfonate were calculated at 23 $\mu$g/ml and 35 $\mu$g/ml, respectively. Polystyrene sulfonate completely inhibits infectivity of human fallopian tube tissue by gonococci at 100 $\mu$g/ml. $PS_{53}$ had only a small effect on gonococcal multiplication at concentrations up to about 0.1 mg/ml. However, growth was inhibited by about 96 percent at 1 mg/ml. Infectivity of human fallopian tube tissue by gonococci was completely inhibited by $PS_{53}$ at 1 mg/ml. Gonococci multiplication was completely inhibited by 100 $\mu$g/ml $H_2SO_4$-modified mandelic acid. The $lC_{50}$ for $H_2SO_4$-modified mandelic acid was about 15–17 $\mu$g/ml.

Example 11

This example illustrates the inhibitory effect of several of the inhibitory agents of this invention on *Chlamydia trachomatis* using a multiplication assay. Immediately before the assay, cryopreserved *Chlamydia trachomatis* (serotype E/UW-5/CS) samples were quickly thawed at 37° C. and suspended in Hank's balanced salt solution (HBSS) by mild sonication. Serial 1:10 dilutions ($10^{-1}$ to $10^{-7}$) of the bacterial suspension were made. HeLa monolayers on coverslips were inoculated with 100 $\mu$l of the chlamydia samples in the presence (0.1, 1.0, 10, 100, and 1000 $\mu$g/ml) or absence of the test agents. After one hour, the monolayers were washed with HBSS to remove free chlamydia and test agent (if present) and then incubated for 48 hours in HBSS at 37° C.

After the medium was removed, the HeLa monolayer samples were fixed in methanol and washed. The cells were then treated with Kallsted Chlamydia Culture Confirmation fluorescein-conjugated Monoclonal Antibody for 30 minutes at room temperature in a dark, humidified chamber. The cells were then washed with water and covered with coverslip using a mounting medium. Inclusions due to chlamydia infection were visualized with a fluorescent microscope as green fluorescence.

Phosphorylated hesperidin inhibited chlamydia multiplication by about 90 percent at a level of 100 $\mu$g/ml. Sulfonated hesperidin was moderately effective in inhibiting chlamydia multiplication. The $IC_{50}$ for sulfonated hesperidin was about 100 $\mu$g/ml. A two-log (90 percent) reduction is calculated to occur at about 298 mg/ml. Polystyrene sulfonate completely inhibited chlamydia multiplication at 1 mg/ml. $PS_{53}$ at 1 mg/ml inhibited chlamydia multiplication by approximately 95 percent. The $H_2SO_4$-modified mandelic acid had an $IC_{50}$ of 0.05 $\mu$g/ml.

Example 12

This example illustrates the contraceptive effect of $H_2SO_4$-modified mandelic acid. Rabbit spermatozoa were collected and then diluted in a TALP buffer containing glucose, lactate, and pyruvate. Test compounds were dissolved in the same buffer system. Sperm were incubated for about 15 minutes at 37° C. with and without added $H_2SO_4$-modified mandelic acid. Female rabbits were then artificially inseminated with about 0.5 ml of buffer containing about 22.5–30×$10^6$ sperm. For controls (i.e., sperm and buffer containing no added contraceptive agents), fertilization averaged about 96 percent. With 5 mg/ml of $H_2SO_4$-modified mandelic acid added to the sperm/buffer mixture, fertilization fell to an average of about 10 percent. The $H_2SO_4$-modified mandelic acid did not effect sperm motility.

The embodiments and examples described and discussed above are intended to illustrate the present invention and not to limit the scope of the invention which is defined in the appended claims.

That which is claimed is:

1. A method for protecting two or more parties engaged in sexual activity from transmission and infection by a sexually transmitted disease, said method comprising applying an effective amount of a protective agent to an area of the body to be engaged in the sexual activity of at least one of the parties prior to the sexual activity and then engaging in the sexual activity, wherein the protective agent is a dimer of mandelic acid or a dimer of substituted mandelic acid.

2. A method as defined in claim 1, wherein the protective agent is contained in an inert carrier.

3. A method as defined in claim 2, wherein the protective agent is at a concentration greater than about 5 mg/g.

4. A method as defined in claim 3, wherein the protective agent is at a concentration of about 10 to 200 mg/g.

5. A method for protecting two or more parties engaged in sexual activity from transmission and infection by a sexually transmitted disease, said method comprising administering an effective amount of a protective agent to the area or areas of body of one or more of the parties in sexual contact during the sexual activity before or after the sexual activity, wherein the protective agent is a dimer of mandelic acid or a dimer of substituted mandelic acid.

6. A method as defined in claim 5, wherein the protective agent is contained in an inert carrier.

7. A method as defined in claim 6, wherein the protective agent is at a concentration greater than about 5 mg/g.

8. A method as defined in claim 7, wherein the protective agent is at a concentration of about 10 to 200 mg/g.

9. A method for protecting two or more parties engaged in sexual activity from transmission and infection by a sexually transmitted disease through sexual activity, said method comprising applying an effective amount of a protective agent to an area or areas of the body to be engaged in the sexual activity of at least one of the parties prior to the sexual activity, then engaging in the sexual activity, and then applying an additional amount of the protective agent to the area or areas which was engaged in the sexual activity, wherein the protective agent is a dimer of mandelic acid or a dimer of substituted mandelic acid.

10. A method as defined in claim 9, wherein the protective agent is contained in an inert carrier.

11. A method as defined in claim 10, wherein the protective agent is at a concentration greater than about 5 mg/g.

12. A method as defined in claim 11, wherein the protective agent is at a concentration of about 10 to 200 mg/g.

13. A method for protecting two parties engaged in sexual activity from transmission and infection by a sexually transmitted disease through sexual activity between the two parties wherein the first party is a male and the second party is a male or female and the sexual activity involves the penis of the first party, said method comprising applying a condom to the penis of the first party, applying an effective amount of a protective agent to an area of the body of the second party which is to be engaged in the sexual activity or to the condom of the first party prior to the sexual activity, and then engaging in the sexual activity, wherein the protective agent is a dimer of mandelic acid or a dimer of substituted mandelic acid.

14. A method as defined in claim 13, wherein the protective agent is contained in an inert carrier.

15. A method as defined in claim 14, wherein the protective agent is at a concentration greater than about 5 mg/g.

16. A method as defined in claim 15, wherein the protective agent is at a concentration of about 10 to 200 mg/g.

17. A method for protecting an uninfected individual from transmission of a sexually transmitted disease to the uninfected individual through contact with the bodily fluids of a potentially sexually transmitted disease infected person, said method comprising applying to the body or portion of the body of the uninfected individual an effective amount of protective agent at a time prior to likely contact with the bodily fluids or at a time as soon as possible after actual contact with the bodily fluids, wherein the protective agent is a dimer of mandelic acid or a dimer of substituted mandelic acid.

18. A method as defined in claim 17, wherein the sexually transmitted disease is HIV/AIDS.

19. A method as defined in claim 18, wherein the protective agent is contained in a water-based carrier and wherein the protective agent is applied by flooding the body or portion of the body with the carrier containing the protective agent.

20. A method as defined in claim 18, wherein the protective agent is applied before likely contact and, if contact occurs, is reapplied after actual contact.

21. A method as defined in claim 19, wherein the protective agent is applied before likely contact and, if contact occurs, is reapplied after actual contact.

22. A method for preventing or reducing the risk of pregnancy through sexual activity between a male and a female, said method comprising applying an effective amount of a dimer of mandelic acid or a dimer of substituted mandelic acid to either the male or female in such a manner that sperm from the male are exposed to the dimer of mandelic acid or the dimer of substituted mandelic acid before they can contact the egg or eggs of the female, wherein the exposure to the dimer of mandelic acid or the dimer of substituted mandelic acid is for a sufficient time to prevent or reduce the risk of pregnancy.

23. A method as defined in claim 22, wherein the dimer of mandelic acid or the dimer of substituted mandelic acid is contained in an inert carrier at a concentration greater than about 5 mg/g.

24. A method as defined in claim 23, wherein the dimer of mandelic acid or the dimer of substituted mandelic acid is at a concentration of about 10 to 200 mg/g.

25. A method as defined in claim 12, wherein said method further comprises the use of a male or female condom.

26. A method for protecting two or more parties engaged in sexual activity from transmission and infection by a sexually transmitted disease through sexual activity between the two or more parties, said method comprising applying an effective amount of a protective agent to an area of the body to be engaged in the sexual activity of at least one of the parties prior to the sexual activity and then engaging in the sexual activity, wherein the protective agent is a dimer of mandelic acid or a dimer of substituted mandelic acid of general formula:

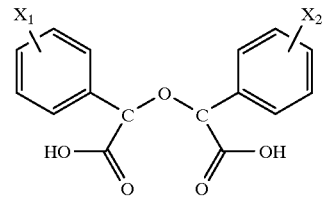

where $X_1$ and $X_2$ are independently selected from the group consisting of —OH, —OR, or halide radicals where R is an alkyl or substituted alkyl radical having from 1 to 6 carbon atoms or an aryl or substituted aryl radical; and wherein the dimer is prepared by reacting mandelic acid or substituted mandelic acid with sulfuric acid at low temperatures and then collecting the dimer.

* * * * *